United States Patent
Neri et al.

[11] Patent Number: 5,714,380
[45] Date of Patent: Feb. 3, 1998

[54] CLOSED VESSEL FOR ISOLATING TARGET MOLECULES AND FOR PERFORMING AMPLIFICATION

[75] Inventors: Bruce P. Neri, North Andover, Mass.; John S. Curtis, Fairlight, England; Mark L. Collins, Holden, Mass.; Danahey Ryan, Port Deposit, Md.

[73] Assignee: Amoco Corporation, Chicago, Ill.

[21] Appl. No.: 622,491

[22] Filed: Mar. 25, 1996

Related U.S. Application Data

[63] Continuation of Ser. No. 400,657, Mar. 8, 1995, abandoned, which is a continuation of Ser. No. 257,469, Jun. 8, 1994, abandoned, which is a continuation of Ser. No. 124,826, Sep. 21, 1993, abandoned, which is a continuation of Ser. No. 946,749, Sep. 17, 1992, abandoned, which is a continuation of Ser. No. 648,468, Jan. 31, 1991, abandoned, which is a continuation-in-part of Ser. No. 644,967, Jan. 22, 1991, abandoned, which is a continuation of Ser. No. 136,920, Dec. 21, 1987, abandoned, which is a continuation-in-part of Ser. No. 922,155, Oct. 23, 1986, abandoned.

[51] Int. Cl.$^6$ ............................ C12M 1/34; C12M 1/40
[52] U.S. Cl. ............................ 435/287.2; 435/287.6; 435/288.5; 435/288.7; 422/68.1; 422/102
[58] Field of Search ............................ 435/286.5, 287.1, 435/287.2, 287.6, 287.9, 288.5, 288.6, 288.7, 304.2, 305.2, 810; 422/61, 68.1, 55, 58, 99, 102; 141/329, 330

[56] References Cited

U.S. PATENT DOCUMENTS

| | | | |
|---|---|---|---|
| 3,036,894 | 5/1962 | Forestiere | 23/230 |
| 3,647,227 | 3/1972 | Goldstein et al. | 422/58 |
| 3,666,631 | 5/1972 | Rich et al. | 435/287.6 |
| 3,697,227 | 10/1972 | Goldstein et al. | 422/58 |
| 3,807,467 | 4/1974 | Tascher et al. | 141/329 |
| 4,007,010 | 2/1977 | Woodbridge, III | 422/50 |
| 4,038,150 | 7/1977 | Dorn et al. | 435/288.2 |
| 4,210,623 | 7/1980 | Breno et al. | 141/330 |
| 4,390,499 | 6/1983 | Curtis et al. | 422/102 |
| 4,647,541 | 3/1987 | Guadagno et al. | 422/56 |
| 4,654,127 | 3/1987 | Baker et al. | 422/68 |
| 4,657,869 | 4/1987 | Richards et al. | 435/287 |
| 4,665,034 | 5/1987 | Chandler | 435/810 |
| 4,673,657 | 6/1987 | Christian | 422/58 |
| 4,690,801 | 9/1987 | Anderson | 422/68.1 |
| 4,753,775 | 6/1988 | Ebersole et al. | 422/81 |

(List continued on next page.)

FOREIGN PATENT DOCUMENTS

| | | |
|---|---|---|
| 0 381 501 | 8/1990 | European Pat. Off. . |
| 0381501 | 8/1990 | European Pat. Off. . |
| 0 435 380 | 7/1991 | European Pat. Off. . |
| 0 482 713 | 4/1992 | European Pat. Off. . |

OTHER PUBLICATIONS

Dynabeck®, DNA Technology, product brochure, 1989.
Kwok et al., *Nature*, 339:237–238 (1989).
Ulber, *Nature*, 340:733–734, (1989).

*Primary Examiner*—William H. Beisner
*Attorney, Agent, or Firm*—Norval B. Galloway

[57] ABSTRACT

The present invention features a vessel for isolating a target in a sample. The vessel includes at least one reaction chamber, a wash system and an effluent system. The reaction chamber includes a closed cell adapted to receive a support, a sample potentially containing target and at least one first probe, and thereafter being closed. The probe is capable of associating with the support and the target to form a support-probe-target complex and sample debris upon imposition of probe binding conditions within the reaction chamber. A wash system is capable of introducing solutions into the reaction chamber for washing the support to solubilize and suspend sample debris. Upon imposition of wash conditions, solutions are allowed to enter the reaction chamber to solubilize such sample debris. An Effluent system is in communication with the reaction chamber and capable of receiving sample debris and wash solutions. The vessel receives the sample, binds the target, if present, to the support, allows wash solutions to remove sample debris, and removes wash solutions and sample debris through the effluent system, leaving target isolated on the support.

20 Claims, 3 Drawing Sheets

U.S. PATENT DOCUMENTS

| | | | |
|---|---|---|---|
| 4,786,600 | 11/1988 | Kramer et al. | 435/235 |
| 4,859,421 | 8/1989 | Apicella | 422/61 |
| 4,963,663 | 10/1990 | White et al. | 435/61 |
| 4,965,047 | 10/1990 | Hammond | 422/5 E |
| 4,978,502 | 12/1990 | Dole et al. | 422/58 |
| 5,061,446 | 10/1991 | Guigan | 422/102 |
| 5,089,232 | 2/1992 | DeVaney et al. | 206/219 |
| 5,089,233 | 2/1992 | Devoney, Jr. et al. | 422/99 |
| 5,154,888 | 10/1992 | Zander et al. | 422/58 |
| 5,160,702 | 11/1992 | Kopf et al. | 422/72 |
| 5,288,463 | 2/1994 | Chemelli | 422/102 |

CLOSED VESSEL FOR ISOLATING TARGET MOLECULES AND FOR PERFORMING AMPLIFICATION

This application is a continuation of U.S. Ser. No. 08/400,657, filed Mar. 8, 1995, now abandoned, which is a continuation of U.S. Ser. No. 08/257,469, filed Jun. 8, 1994, now abandoned, which is a continuation of U.S. Ser. No. 08/124,826, filed Sep. 21, 1993, now abandoned, which is a continuation of U.S. Ser. No. 07/946,749, filed Sep. 17, 1992, now abandoned, which is a continuation of U.S. Ser. No. 07/648,468, filed Jan. 31, 1991, now abandoned, which is a continuation-in-part of U.S. Ser. No. 07/644,967, filed Jan. 22, 1991, now abandoned, which is a continuation of U.S. Ser. No. 07/136,920, filed Dec. 21, 1987, now abandoned, which is a continuation-in-part of U.S. Ser. No. 06/922,155, filed Oct. 23, 1986 now abandoned.

The present invention pertains to methods reagents, compositions, kits, and instruments for use in capturing target molecules. One embodiment of the present invention features a substantially closed containment vessel for capturing deoxyribonucleic acid (DNA) or ribonucleic acid (RNA) from clinical samples. Further embodiments of the present invention feature a closed containment vessel for detecting the formation of nucleic acid hybridization reactions and for amplifying signals related to such hybridization reactions. Embodiments of the present invention provide methods and articles of manufacture for rapid, sensitive detection of target molecules in clinical samples.

The following definitions are provided to facilitate an understanding of the present invention. The term "biological binding pair" as used in the present application refers to any pair of molecules which exhibit natural affinity or binding capacity. For the purposes of the present application, the term "ligand" will refer to one molecule of the biological binding pair and the term "antiligand" or "receptor" will refer to the opposite molecule of the biological binding pair. For example, without limitation, embodiments of the present invention have applications in nucleic acid hybridization assays where the biological binding pair includes two complementary strands of polynucleic acid. One of the strands is designated the ligand and the other strand is designated the antiligand. However, the biological binding pair may include antigens and antibodies, proteins and protein binders, chelators, drugs, and drug receptor sites and enzymes and enzyme substrates.

The term "probe" refers to a ligand of known qualities capable of selectively binding to a target antiligand. As applied to nucleic acids, the term "probe" refers to a strand of nucleic acid having a base sequence complementary to a target strand.

The term "label" refers to a molecular moiety capable of detection including, by way of example, without limitation, radioactive isotopes, enzymes, luminescent agents, and dyes. The term "agent" is used in a broad sense, including any molecular moiety which participates in reactions which lead to a detectable response. The term "cofactor" is used broadly to include any molecular moiety which participates in reactions with the agent.

The term "retrievable" is used in a broad sense to describe an entity which can be substantially dispersed within a medium and removed or separated from the medium by immobilization, filtering, binding, partitioning, or the like.

The term "support" when used alone includes conventional supports such as filters and membranes as well as retrievable solid supports.

The term "reversible," in regard to the binding of ligands and antiligands, means capable of binding and releasing upon changes in the environment which do not permanently alter the gross chemical nature of the ligand and antiligand. For example, without limitation, reversible binding of nucleic acid ligands and antilands is controlled by changes in the pH, temperature, and ionic strength which do not destroy the ligand or antiligand.

The term "amplify" is used in the broad sense to mean creating an amplification product which may include by way or example, additional target molecules, or target-like molecules which are capable of functioning in a manner like the target molecule, or a molecule subject to detection steps in place of the target molecule, which molecules are created by virtue of the presence of the target molecule in the sample. In the situation where the target is a polynucleotide, additional target, or target-like molecules, or molecules subject to detecting can be made enzymatically with DNA or RNA polymerases or transcriptases.

The terms "closed" and "contained" are used to suggest that reactions with respect to a sample do not share physical hardware, with which reactants may come in contact, with any other sample, and such reactions are performed in an atmosphere unique to such sample and reactants.

Genetic information is stored in living cells in threadlike molecules of DNA. In vivo, the DNA molecule is a double helix, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand.

DNA consists of covalently linked chains of deoxyribonucleotides. RNA consists of covalently linked chains of ribonucleotides. The genetic code of a living organism is carried upon DNA in the sequence of the base pairs. Living organisms use RNA to transcribe and translate the genetic code into proteins.

Each nucleic acid is linked by a phosphodiester bridge between the five prime hydroxyl group of the sugar of one nucleotide and the three prime hydroxyl group of the sugar of an adjacent nucleotide. Each linear strand of naturally occurring DNA or RNA has one terminal end having a free five prime hydroxyl group and another terminal end having a three prime hydroxyl group. The terminal ends of polynucleotides are often referred to as being five prime termini or three prime termini in reference to the respective free hydroxyl group. Complementary strands of DNA and RNA form antiparallel complexes in which the three prime terminal end of one strand is oriented to the five prime terminal end of the opposing strand.

Nucleic acid hybridization assays are based on the tendency of two nucleic acid strands to pair at complementary regions. Presently, nucleic acid hybridization assays are primarily used to detect and identify unique DNA or RNA base sequences or specific genes in a complete DNA molecule, in mixtures of nucleic acid, or in mixtures of nucleic acid fragments.

The identification of unique DNA or RNA sequences of specific genes within the total DNA or RNA extracted from tissue or culture samples may indicate the presence of physiological or pathological conditions. In particular, the identification of unique DNA or RNA sequences or specific genes, within the total DNA or RNA extracted from human or animal tissue, any indicate the presence of genetic diseases, of conditions such as sickle cell anemia, tissue compatibility, cancer and precancerous states, or bacterial or vital infections. The identification of unique DNA or RNA sequences or specific genes within the total DNA or RNA extracted from bacterial cultures or tissue containing bacteria may indicate the presence of antibiotic resistance, toxins, viruses, or plasmids, or provide identification between types of bacteria.

Thus, nucleic acid hybridization assays have great potential in the diagnosis and detection of disease. Further potential exists in agriculture and food processing where nucleic acid hybridization assays may be used to detect plant pathogenesis or toxin-producing bacteria.

One of the most widely used nucleic acid hybridization assay procedures is Knows as the Southern blot filter hybridization method or simply, the Southern procedure (Southern, E., *J. Mol. Biol. 1*, 98,503, 1975). The Southern procedure is used to identify target DNA or RNA sequences. This procedure is generally carried out by immobilizing sample RNA or DNA to nitrocellulose sheets. The immobilized sample RNA or DNA is contacted with radio-labeled probe strands of DNA having a base sequence complementary to the target sequence carrying a radioactive moiety which can be detected. Hybridization between the probe and the sample DNA is allowed to take place.

The hybridization process is generally very specific. The labeled probe will not combine with sample DNA or RNA if the two nucleotide entities do not share substantial complementary base pair organization standard. Hybridization can take from three to 48 hours depending on given conditions.

To the extent possible, unhybridized DNA probe is subsequently washed away. However, as a practical matter there is always nonspecific binding of the labeled probe to supports which appears as "background noise" on detection. Background noise reduces the sensitivity of an assay. The nitrocellulose sheet is placed on a sheet of X-ray film and allowed to expose. The X-ray film is developed with the exposed areas of the film identifying DNA fragments which have been hybridized to the DNA probe and therefore have the base pair sequence of interest.

The use of radioactive labeling agents in conjunction with Southern assay techniques have allowed the application of nucleic acid assays to clinical samples. Radioactive decay is detectable even in clinical samples containing extraneous proteinaceous and organic material. However, the presence of extraneous proteinaceous and organic material may contribute to nonspecific binding of the probe to the solid support. Moreover, the use of radioactive labeling techniques requires a long exposure time to visualize bands of X-ray film. A typical Southern procedure may require 1 to 7 days for exposure. The use of radioactive labeling agents further required special laboratory procedures and licenses.

The above problems associated with assays involving radioisotopic labels have led to the development of techniques employing nonisotopic labels. Examples of nonisotopic labels include enzymes, luminescent agents, and dyes. Luminescent labels emit light upon exitation by an external energy source and may be grouped into categories dependent upon the source of the exciting energy, including: radioluminescent labels deriving energy from high energy particles; chemiluminescent labels which obtain energy from chemical reactions; bioluminescent labels wherein the exciting energy is applied in a biological system; and photoluminescent or fluorescent labels which are excitable by units of electromagnetic radiation (photons) of infrared, visual or ultraviolet light. See, generally, Smith et al., *Ann. Clin. Biochem.*, 18:253 274 (1981).

Nonisotopic assay techniques employing labels excitable by nonradioactive energy sources avoid the health hazards and licensing problems encountered with radioisotopic label assay techniques. Moreover, nonisotopic assay techniques hold promise for rapid detection avoiding the long exposure time associated with the use of X-ray film.

However, nonisotopic assays have not conveyed the sensitivity or specificity to assay procedures necessary to be considered reliable. In luminescent assays, the presence of proteins and other molecules carried in biological samples may cause scattering of the exciting light or may absorb light in the spectrum of emission of the luminescent label, resulting in a quenching of the luminescent probe.

In enzymatic assays, the presence of proteins and other molecules carried in biological samples may interfere with the activity of the enzyme.

Similarly, in colorimetric assays, the change in color may not be detectable over proteins and other materials carried in biological samples.

Additionally, the time period for hybridization in Southern-like procedures may be unacceptable for some applications. The use of a two probe systems to effect target capture on conventional non-retrievable supports has been suggested in an article authored by Ann-Christine Syu̇änen, Matti Laaksonen and Hans Söderlund entitled "Fast Quantification of Nucleic Acid Hybrids by Affinity-Based Hybrid Collection;" *Nucleic Acids Research*, 14(12):5037 (1986), and U.S. Pat. No. 4,751,177 to Stabinsky. The interest in multiple probe systems is in part an effort to improve the Kinetics of hybridization.

Copending application U.S. Ser. No. 922,155, filed Oct. 23, 1986, now abandoned, addresses issues of background, hybridization kinetics and kinetics with regard to binding target to supports. One embodiment of the invention of U.S. Ser. No. 922,155 comprises a method for isolating target. By way of example, without limitation, one method comprises contacting a sample medium potentially containing target molecules with probes and a first support associated or capable of associating with at least one probe under binding conditions. The probes are capable of selectively reversibly binding to the target molecule to form a complex including the probe target and the first retrievable support. Next, the support is separated from the sample medium and brought into contact with a second medium. Next, the support is subjected to releasing conditions to release the target from the support and the support is separated from the second medium. Next, a second support is contacted with the second medium under binding conditions. The second support is associated with or capable of associating with at least one probe capable of selectively binding to the target molecule. Under binding conditions, the target forms a complex with the probe associated to second support for further processing.

Embodiments described in U.S. Ser. No. 922,1555 feature a first support which is retrievable in the sense that it is capable of substantially homogeneous dispersion within the sample medium and can be substantially physically separated retrieved, or immobilized within the sample medium.

Separation of the first support from the first medium removes nonspecifically bound cellular debris attached to the first support. Further binding of the target molecule to a second support further concentrates the target for detection and permits further release-capture cycles for greater purification.

The binding or capture and subsequent release of a target for further processing is sometimes referred to as reversible target capture or RTC. One such capture and release is sometimes referred to as a cycle of RTC.

Powerful amplification techniques give rise to special problems. In some amplification chemistries, a single molecule can trigger a cascade resulting in signal. In an open laboratory environment, such molecules may exist in the environment carried by air or on equipment. Contamination on equipment can lead to sample to sample, and assay to assay carryover. Molecules which are carried in the air due to microdroplets and turbulence can give rise to spurious results which are perhaps acceptable for research purposes but problematic for clinical applications. Open automated instrumentation, running countless assay procedures, may quickly become contaminated with such molecules and become inaccurate in their performance.

SUMMARY OF THE INVENTION

Embodiments of the present invention feature a vessel for isolating target from a sample and for performing amplification, in a closed environment. Embodiments of the present invention are well suited for performing diagnostic procedures for detecting target molecules.

One embodiment of the present invention features a vessel for isolating target in a sample. The vessel comprises at least one reaction chamber, wash means and effluent means. The reaction chamber comprises a closed cell adapted to receive a support, a sample potentially containing target and at least one first probe, and thereafter being closed. The probe is capable of associating with the support and the target to form a support-probe-target complex and sample debris upon imposition of probe binding conditions within the reaction chamber. Wash means are capable of introducing solutions into the reaction chamber for washing the support to solubilize and suspend sample debris. Upon imposition of wash conditions, solutions are allowed to enter the reaction chamber to solubilize such sample debris. Effluent means are in communication with the reaction chamber and capable of receiving sample debris and wash solutions. The vessel receives the sample, binds the target, if present, to the support, allows wash solutions to remove sample debris, and removes wash solutions and sample debris through effluent means, leaving target isolated on the support.

One embodiment of the present invention features wash means which comprise at least one wash chamber and at least one wash communication means. The wash chamber comprises a closed cell adapted to hold solutions in a closed environment for introduction into the reaction chamber. Wash communication means are interposed between the reaction chamber and the wash chamber to maintain such chambers and solutions separate until imposition of wash communication conditions. Upon imposition of wash communication conditions, solutions held in the wash chamber are allowed to enter the reaction chamber to solubilize and suspend sample debris. The wash chamber allows the vessel to be more self contained.

A still further embodiment of the present invention features effluent means comprising at least one effluent chamber and at least one effluent communication means. The effluent chamber comprises a compartment for receiving solutions from the reaction chamber. Effluent communication means are interposed between the reaction chamber and the effluent chamber and are capable of maintaining fluid in the effluent chamber and the reaction chamber substantially separate until the imposition of effluent communication conditions. By way of example, without limitation, one embodiment features effluent communication means comprising a passage, which passage is capable of cooperating with external clamps to restrict or open the passage.

A further embodiment of the present invention features a plurality of reaction chambers, wash means, effluent means, eluent means, and at least one reaction chamber communication means. The plurality of reaction chambers comprise a first reaction chamber and a second reaction chamber. The first reaction chamber comprises a closed cell adapted to receive the support, sample potentially containing target, and probe. After receiving the support, sample and probe, the first reaction chamber is capable of being closed. The probe is capable of binding to target to form a probe-target complex upon imposition of release conditions. Wash means are capable of introducing wash solutions into the first reaction chamber upon imposition of wash communication conditions to remove sample debris. Effluent means are capable of receiving sample debris and wash solutions from the first reaction chamber. Eluent means are capable of introducing solutions into the first reaction chamber upon imposition of eluent communication conditions at which eluent solutions held in the eluent chamber are allowed to enter the first reaction chamber to solubilize the probe-target complex. The second reaction chamber is comprised of a closed cell adapted to receive the eluent solution from the first reaction chamber. Reaction chamber communication means are interposed between the first and second reaction chambers and capable of maintaining the first and second reaction chambers separate until imposition of reaction chamber communication conditions at which time solutions held in the first reaction chamber are allowed to enter the second reaction chamber, leaving behind the support. The vessel allows a first reaction chamber to receive sample, and bind target to support, remove sample debris, and release target from the support for collection in the second reaction chamber.

With an emphasis on diagnostic application, one embodiment of the present invention features at least one reaction chamber which is capable of receiving a detection probe. The detection probe is capable of binding to target to form a detection probe-target complex the presence of which can be detected.

Similarly, for diagnostic applications, a further embodiment of the present invention features a read chamber and read chamber communication means. The read chamber comprises a closed cell having read surfaces. The read chamber is capable of receiving solutions from a reaction chamber, which solutions, in the event target is present in the sample, are capable of producing a detectable response. The read surfaces are capable of transmitting such detectable response to the exterior of the vessel. The read chamber communication means is interposed between the read chamber and the reaction chamber and capable of maintaining the read chamber and the reaction chamber separate until imposition of read communication conditions. Upon imposition of read communication conditions, solutions held in the reaction chamber are allowed to enter the read chamber for detection purposes.

In one embodiment in the present invention, the read chamber is adapted to hold detection reagents. The detection reagents allow the detection probe to produce a detectable response in the event target is or was present in the sample. One such detection reagent includes the enzyme Q-Beta Replicase and such other compositions necessary for the replication of MDV-1-like molecules, a 221 base RNA ribonucleic acid which self replicates in the presence of the enzyme.

In one embodiment, the detection reagents are held in one or more reagent chambers. Each reagent chamber comprising a closed cell which is opened to the read chamber upon imposition of read communication conditions.

In order to facilitate loading the vessel, one embodiment of the present invention features a vessel having at least one sample well and at at least one sample communication means. The sample well is adapted for receiving sample and comprises an open container adapted to receive sample. The sample well is capable of cooperating with cap means to close the sample well. The sample well communication means is capable of transporting the sample to the reaction chamber upon imposition of sample communication conditions. One embodiment features sample well communication means comprising a passage to the reaction chamber.

One embodiment of the present invention features a vessel having sample well housing, cap means and a closure plug. The sample well housing is an open container having receiving surfaces for a cap housing. The sample well housing defines open container adapted to receive sample, and cooperates with sample communication means to transport sample to the reaction chamber. Cap means comprise a cap housing capable of being slidably received in the sample well housing. The cap housing defines an open container having two ends, one of the ends having a breakable wall, and the other adapt end adapted to receive the closure plug. The closure plug is adapted to fit and seal the open end of the cap housing to contain the sample in a closed environment. The cap housing end having the breakable wall is adapted to be slidably received by the sample well housing and wherein the breakable wall breaks, to release sample into the reaction chamber.

A further embodiment of the present invention features at least one probe well and at least one probe communication means. The probe well comprises a housing defining a container adapted to receive probe. The probe housing is capable of cooperating with probe cap means to close the probe well. The probe communication means is capable of transporting probe to the reaction chamber upon imposition of probe communication conditions.

In one embodiment, the probe cap means comprises a probe cap housing capable of being slidably received by the probe well housing. The probe cap housing defines a closed container having one end having a breakable wall which end having the breakable wall is adapted to be received by probe well housing. Upon imposition of probe communication conditions, the probe well housing breaks the breakable wall to release probe.

A further embodiment of the present invention features a single probe-sample cap which includes features of the probe cap and sample cap. The single probe-sample cap allows the remaining part of the vessel to be generic for a variety of tests. Thus, the probe-sample cap can be loaded with probes in a manufacturing process specific for a particular assay. A technician, nurse or physician would load the sample into the probe-sample cap housing and close the housing with the closure plug. The sample-probe cap would be fitted to the remaining vessel. The remaining vessel can be made generic and applicable for a variety of assays. Only the probes need to be modified for each test. Preferably, each cap and remaining vessel will have identification means such as coding bars for the type of assay and provision for the name of the patient or the nature of the test and date.

Embodiments of the present invention are easily manufactured from plastic film. Preferably, the chambers and features of the vessel are formed by welding two films of plastic. The preferred plastic film is manufactured by DuPont de NeMours and sold under the tradename Surlyn®. Surlyn® is an ionomer resin thermoplastic containing both covalent and ionic bonds. The ionic intercharge electrostatic forces are very powerful and thermally reversible at temperatures varying from 175° C. to 290° C. Two films of Surlyn® plastic can be placed together during the manufacturing process with one of the films heat-formed to the shape required on a continuous speed production process and the second film laid on top. Permanent walls may be formed between the two films to form chambers, passages and seals. In addition, semipermanent walls can be formed to serve as burstable seals.

Walls and seals are made with heated filaments. The duration of heat, compressive pressure exerted on the two films temperature of the filament and cooling time influence the nature of the wall.

Embodiments of the present invention feature various communication means comprised of burstable seals. For example, without limitation, embodiments of the present invention feature wash communication means, reaction cell communication means, eluent communication means, and read communication means. All such communication means can readily be made in Surlyn® plastic to comprise burstable seals between chambers.

In addition, permanent walls can be incorporated within the vessel during the performance of the assay to reclose chambers that have been spent.

Preferred embodiments of the present invention feature a plurality of reaction cells, wash chambers, eluent chambers and effluent chambers to facilitate multiple rounds of reversible target capture leading to a final reading of the assay result in a read chamber.

Embodiments of the present invention allow the performance of target isolation and amplification in a closed environment. Each assay vessel is closed to every other vessel thereby avoiding cross contamination between samples and assays. Embodiments of the present invention feature a vessel which does not require the interaction of any common equipment which would be used in contact with solutions with any other sample. Vessels in accordance with the present invention are suitable for use in instrumentation capable of performing manual functions. To facilitate manual operations, one embodiment of the present invention features a backing plate.

The use of films of Surlyn® and backing plates allows the vessel of the present invention to be readily manufactured in a continuous manner.

Other aspects and advantages of the invention will become apparent upon consideration of the following detailed descriptions with reference to FIGS. 1 through 9, which by way of example, illustrate preferred embodiments of the present invention and the principles thereof, and what is now considered to be the best mode to apply these principles.

DETAILED DESCRIPTION OF THE DRAWINGS

Figure 1:
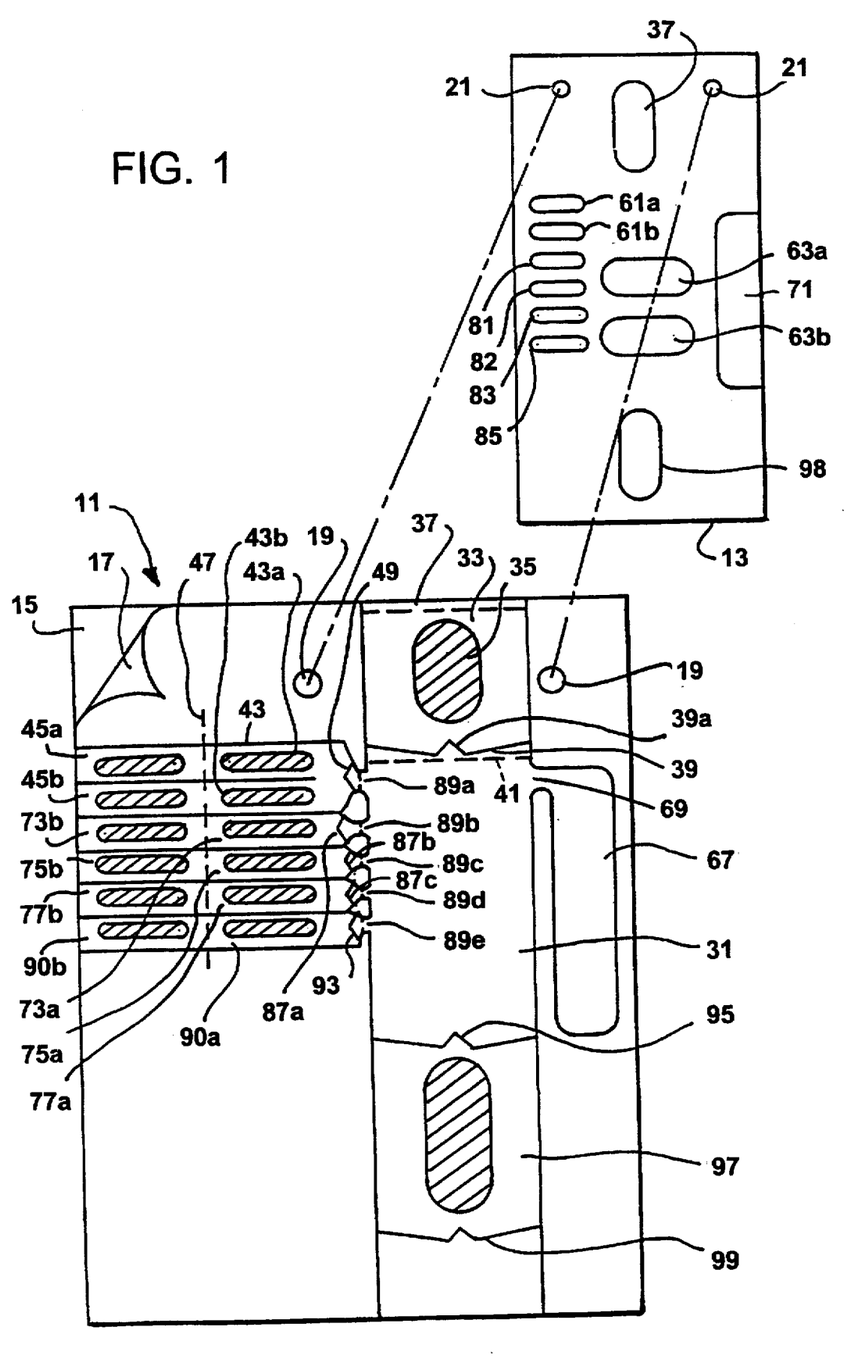
FIG. 1 is a exploded perspective view of a vessel and vacuum plate embodying features of the present invention.

To facilitate discussion of the present invention, reference will be made to FIGS. 1 through 9, which illustrate preferred embodiments of the present invention adapted for use with nucleic acid probes for the detection of nucleic acid targets. Those skilled in the art will recognize the application of the invention for other ligand and antiligand systems as well. Turning first to FIG. 1, FIG. 1 shows, in exploded perspective view, a vessel 11, embodying features of the present invention. The vessel 11 is comprised of the following major elements: a backing plate, generally designated 13, a first sheet of plastic film 15 and a second sheet of plastic film 17. The two sheets of plastic film 15 and 17 are positioned one on top of the other. Alignment holes 19 in the first and second sheets 15 and 17 allow each plastic film to be stably positioned with respect to each other and with respect to the backing plate 13. Backing plate 13 is equipped with holes 21 or, in the alternative pins (not shown) capable of cooperating with holes 19. Adhesive can be used to secure the sheets 15 and 17 with respect to backing plate 13.

The two sheets of plastic film are preferably comprised of Surlyn®. The two sheets of plastic film, 15 and 17, are welded together to form features of the vessel 11. Heavier lines, depicted in FIG. 1, are indicative of permanent seals or walls. Lighter lines are indicative of breakable seals or walls. The difference between breakable seals and permanent walls being one of degree rather than character. Permanent walls tend to retain integrity up to 50–60 psi. Burstable seals tend to rupture at pressures of between 10–30 psi. Such permanent seals or walls are made with a wider filament, which filament is capable of higher temperature, held against the two sheets at higher compressive pressure, for a greater time and cooled more slowly than burstable seals.

The vessel illustrated in FIG. 1 has a first reaction chamber generally designated by numeral 31. The first reaction chamber 31 is adapted to receive a support, a sample potentially containing target, and at least one first probe and thereafter being closed. The probe is capable of associating with the support and the target to form a support-probe-target complex and sample debris upon imposition of probe binding conditions.

As illustrated, sample is introduced into first reaction chamber 31 through sample well 33. Sample well 33 is formed by the first and second sheets of plastic film 15 and 17. The first and second sheets of plastic film are blistered as generally illustrated by the shaded area 35, to provide for additional volume between the two sheets, to accommodate sample. When positioned on the backing plate 13, blister 35 is retained in part by a compartment 37 which allows the first sheet 15 to rest firmly in place.

Probe is added to the sample in the sample well 33 or may be present in the first reaction chamber 31. Addition of probe to sample well 33 allows the probe to form a probe-target complex, prior to binding to support, while the probe and sample are in the sample well 33. After sample has been introduced into the sample well 33, sample well 33 can be sealed to form a closed cell. Dotted line 37' generally represents a permanent seal welded between the first and second sheets of film 15 and 17 after the vessel has received probe and sample.

Following the formation of the permanent seal 37', solutions held in the sample well 33 are urged into the first reaction chamber 31 by sample communication conditions. Sample communication conditions comprise compression of sample well 33 forcing solutions through burstable seal 39. Burstable seal 39 maintains sample well 33 and first reaction chamber 31 separate until sample well 33 is compressed. Burstable seal 3g, as do all burstable seals, includes a point area 39a which point area is directed against the flow of fluid. The point area 39a due to its geometry, creates a weak point in the weld forming burstable seal 39, allowing such seals to break in a consistent manner.

After the fluids have been moved to the reaction chamber 31, a new seal can be welded into the first and second films of plastic 15 and 17 such that fluids cannot reenter the sample well 33. As illustrated, such further weld is generally depicted by dotted line 41 which weld defines the first reaction chamber 31 and forms a closed cell.

In assays which employ a two-probe system, wherein one detection probe is capable of producing a detectable response, and a second capture probe is capable of capturing a detectable probe-target complex to a solid support, it is advantageous to allow the sample and the capture probe to hybridize prior to capture on supports. Capture of the capture probe on the support prior to the capture probe hybridization to target, impairs the kinetics of the binding of probes to target, causing a lower duration in hybridization. The present vessel 11 facilitates hybridization of the probes to the target by maintaining the support separate from the sample during an initial hybridization. Such hybridization may take place in sample well 33 or the first reaction chamber.

Following hybridization, magnetic supports or magnetic beads are preferably received within the first reaction chamber 31. As illustrated, magnetic supports in the form of beads are contained within a support chamber 43. Support chamber 43 is divided into two parts, an upper support chamber, 43a, and a lower support chamber 43b. In order to facilitate the filling of support chamber 43a and 43b, the vessel 11 is equipped with filling chambers 45a and 45b, which allow the vessel 11 to cooperate with filling nozzles, funnels and the like (not shown). After the supports have been loaded into the support chamber 43a and b, the filling chambers 45a and 45b are no longer needed. A permanent seal is welded between the upper and lower plastic sheets at the dotted line 47, sealing the support within the support chambers 43a and 43b which become closed cells. Support chambers 43a and 43b are blistered in order to increase their capacity to hold magnetic supports. Backing plate 13 has indentations 61a and 61b to receive the blisters of support chambers 43a and 43b.

One embodiment of the invention features magnetic supports characterized in their ability to be substantially homogeneously dispersed in a sample medium. Preferably, the magnetic beads carry primary amine or carboxyl functional groups which facilitate covalent binding or association of a probe entity to the magnetic support particles. Preferably, the magnetic support beads are single domain magnets and are superparamagnetic exhibiting no residual magnetism. As described herein, the magnetic support is capable of substantially homogeneous dispersion within the sample medium and includes at least one antiligand moiety capable of binding to a ligand under binding conditions to form a target-probe support complex.

After the target and the probes have been allowed to hybridize under binding conditions within reaction chamber 31, magnetic supports held in support chamber 43a and support chamber 43b are urged into the reaction chamber 31 by imposition of support communication conditions. Support communication conditions include compressing, manually or by equipment, support chambers 43a and 43b to burst the burstable seal 49. Burstable seal 49 is interposed between the magnetic support chamber 43a and 43b and reaction chamber 31 maintaining such chambers separate and apart from each other until such compressive force is exerted on support chambers 43a and 43b. After the magnetic support has entered the reaction chamber 31, support chambers 43a and 43b are sealed from the reaction chamber 31, to avoid fluids backing up into such chambers, by the formation of a permanent seal along dotted line 89a.

The magnetic supports which are now present in reaction chamber 31 are mixed to provide intimate contact and dispersion within the solutions retained in reaction chamber 31. The vessel 11 comprised of flexible plastic films 15 and 17, allows for mixing of solutions by simply rolling across the body of the bag-like structure formed.

The probe-target complex is allowed to bind to the magnetic support, and the magnetic support is immobilized. Backing plate 13 is equipped with hollowed out areas 63a and 63b, towards the back side of the plate to allow the magnets (not shown) used for immobilizing the magnetic supports to be positioned in close proximity to such supports. The use and need for such magnetic support indentations 63a and 63b is dependent upon the thickness of the backing plate 13 and the strength of magnets used for immobilization. During immobilization, sample debris is separated from the target-probe support complex by compressing reaction chamber 31 to urge solutions through effluent passage 69 and into effluent chamber 67. Effluent passage 69 is interposed between the effluent chamber 67 and the first reaction chamber 31. Preferably, effluent passage 69 is kept in a substantially closed position until the imposition of effluent communication conditions. Effluent passage 69 can be maintained in a closed position by compressive clamping pressure on the passage 69 by manual or mechanical means.

Effluent chamber 67 is formed by welding the first and second plastic films 15 and 17 to form a closed cell. Effluent chamber 67 is blistered to accommodate retention of fluids. In order to accommodate the blistered effluent chamber 67, backing plate 13 has an indentation or cutout 71. Following removal of solutions containing sample debris from the first reaction chamber, the magnetic supports and the walls of reaction chamber 31 may contain further nonspecifically bound sample debris. In order to solubilize or suspend such further sample debris, the magnetic supports are further washed.

A series of wash chambers 73a, 75a and 77a are welded into the first and second plastic films. Each wash chamber 73a, 75a and 77a is blistered to accommodate wash solution volumes. Each wash chamber 73a, 75a and 77a has a filling chamber 73b, 75b and 77b respectively. Each filling chamber is also blistered to accommodate nozzles, tubes, funnels and other filling apparatus. (not shown). After the filling operation is complete and fluids are retained within the wash chambers 73a, 75a and 77a, each wash chamber is sealed by the formation of a permanent seal along dotted line 47 to form closed cells.

In order to accommodate the blistered wash chambers 73a, 75a and 77a, backing plate 13 has indentations generally designated by numerals 81, 82 and 83 adapted to receive each blister. Each wash chamber 73a, 75a and 77a, is maintained separate from the reaction chamber 31 by a burstable seal 87a, b and c. Upon imposition of wash communication conditions on the first wash chamber 73a, wash breakable seal 87a opens and allows the solutions retained within the wash chamber 73a to enter the reaction chamber 31. Upon suitable mixing, the magnetic supports are immobilized within the first reaction chamber 31 and the wash solutions removed through effluent passage 69 into effluent chamber 67.

In order to avoid back flow of solutions into any of the open wash chambers 73a, 75a and 77a, each chamber can be sealed after solutions have been removed therefrom by forming a permanent seal along by dotted line 89b, c and d.

Following the wash from the solutions in the first wash chamber 75a, the supports retained in reaction chamber 31 are washed sequentially with the solutions retained in the second wash chamber 75a and, in similar manner, the wash solutions retained in the third wash chamber 77a. During each wash, magnetic supports are retained in the reaction chamber 31 and wash solutions are removed from the reaction chamber 31 by effluent passage 69 into effluent chamber 67.

Preferably, the antiligand system of the support and probe are reversible to allow a probe-target complex to be removed from the magnetic support. Embodiments of the present invention feature complementary homopolymer nucleic acids, ligands and antiligands. One homopolymer nucleic acid is associated with a magnetic particle and a complementary homopolymer nucleic acid is associated with the probe. Such homopolymers can be released upon suitable release conditions such as alterations in temperature, pH, salt strength and the like.

Eluent chamber 90a contains solutions which facilitate dissolution of the target-probe complex from the support. Vessel 11 has an eluent film chamber 90b to facilitate nozzles, funnels, and the like useful for injecting solutions within the eluent chamber 90a. Eluent chamber 90a and eluent filling chamber 90b are formed by welding the first and second plastic films.

After solutions are placed in the eluent chamber 90a, eluent chamber 90a is sealed by the formation of a permanent seal along dotted line 47 to form a closed cell. Eluent filling chamber 90b, as well as wash filling chambers 73b, 75b and 77b, and support filling chamber 45a and 45b are no longer required after filling, for the further functioning of the vessel 11, and can be removed.

Eluent chamber 90a and filling chamber 90b are blistered to accommodate the solutions and filling apparatus (not shown). Backing plate 13 has a cooperating indentation 85 adapted to receive the blister of eluent chamber 90a.

In order to accommodate the blistered area of eluent chamber 90a, backing plate 13 is equipped with an indentation 91.

Eluent chamber 90a is maintained separate from reaction chamber 31 by a burstable seal 93. Upon imposition of eluent communication conditions, burstable seal 93 opens to release the eluent solutions retained within the chamber 90a into reaction chamber 31. Eluent release conditions comprise compressing eluent chamber 90a to urge solutions through the burstable seal 93. In order to prevent such solutions from back-flowing, a permanent seal can be placed by welding the first and second sheets films of plastic 15 and 17 along dotted line 89e. Upon imposition of release conditions, the target-probe complex is released from the support, into the eluent solutions.

The magnetic supports used within the first reaction chamber 31, and the reaction chamber 31 itself, may hold unacceptable levels of nonspecifically bound probe and sample debris. In solution, the target-probe complex is removed from the first reaction chamber 31 through burstable seal 95 into a second reaction chamber 97. The second reaction chamber 97 is formed between welds of the first and second sheets of film 15 and 17. A new permanent seal can be formed about burstable seal 95 to form a closed cell.

Second reaction chamber 97 is blistered to accommodate fluid volumes. Backing plate has an indentation 98 to receive and hold blistered second reaction chamber 97.

The target-probe complex retained within the second reaction chamber 97 can be further processed for detection steps, or amplification, or any other process requiring a substantially isolated target. In the event that such target is desired outside the vessel, a final burstable seal 99 is opened for removal of the contents of the second reaction chamber 97.

Further processing of the target-probe complex may include additional cycles of reversible target capture. A further embodiment of the present invention features four reversible target cycles.

Figures 2, 4:
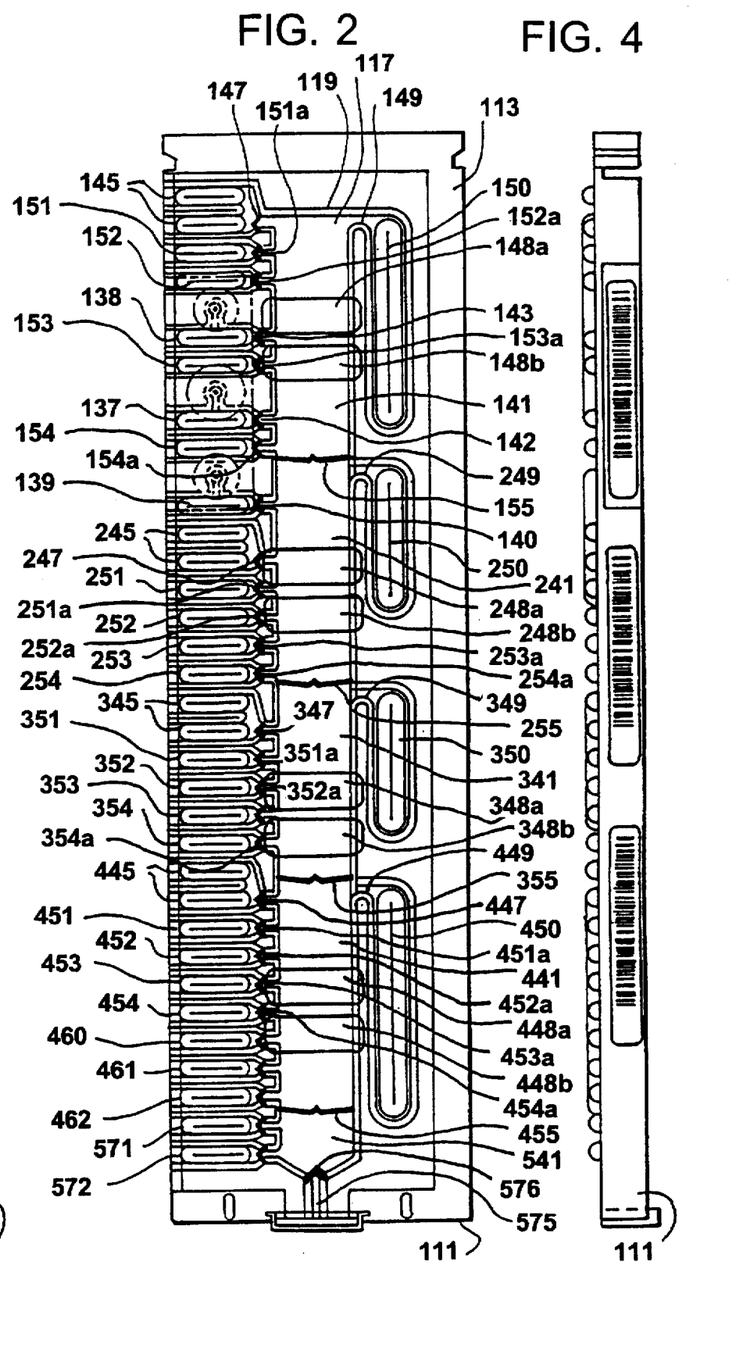
FIG. 2 is a vessel embodying features of the present invention adapted to receive a sample and perform four cycles of reversible target capture and produce a detectable response in the presence of target.
FIG. 4 is a side perspective view of the vessel of FIG. 2.
Figure 3:
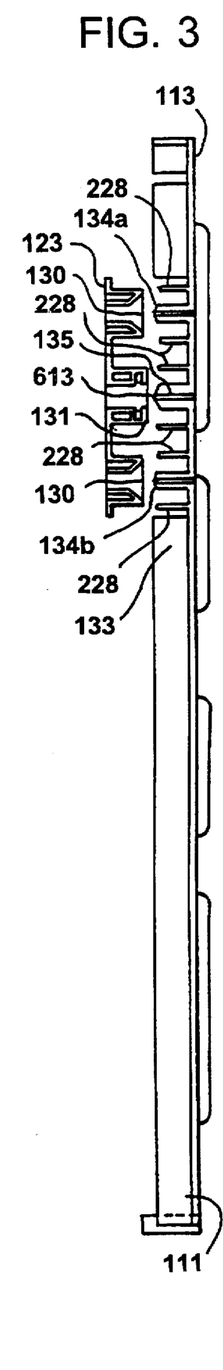
FIG. 3 is a sectional side view of the vessel of FIG. 2 illustrating the cooperation between a sample-probe cap and a sample and probe housings embodying features of the present invention.
Figure 5:
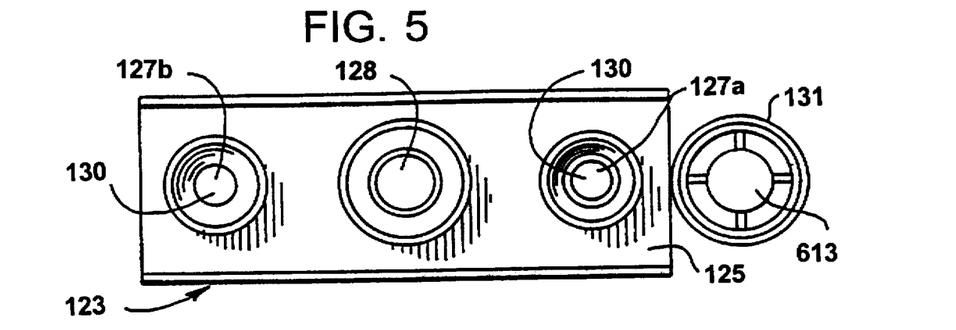
FIG. 5 is a top perspective view of the sample-probe cap embodying of FIG. 2.

FIGS. 2 through 4 illustrate a vessel generally designated by the numeral 111 embodying features of the present invention. The vessel 111 is comprised of the following major elements: a backing plate 113, a first sheet of plastic film 115, a second sheet of plastic film 117, and a cap 123. The first sheet of plastic film 115 is positioned underneath a second plastic sheet 117 in FIG. 2 and, therefore, is obscured from view.

The relationship of cap 123 to the backing plate 113, can best be seen in FIG. 3. The cap 123 is illustrated in greater detail in FIGS. 5 through 8.

Figure 6:
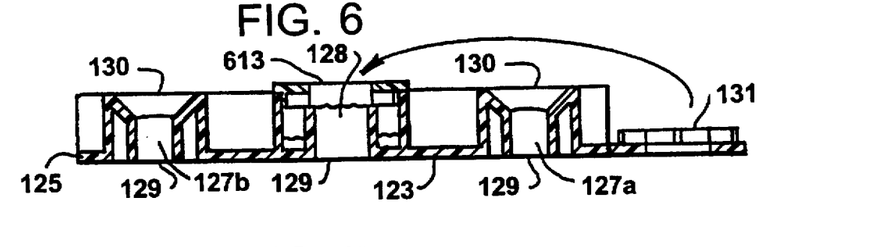
FIG. 6 is a side cross-sectional view of the sample-probe cap illustrated in FIG. 5.
Figure 7:
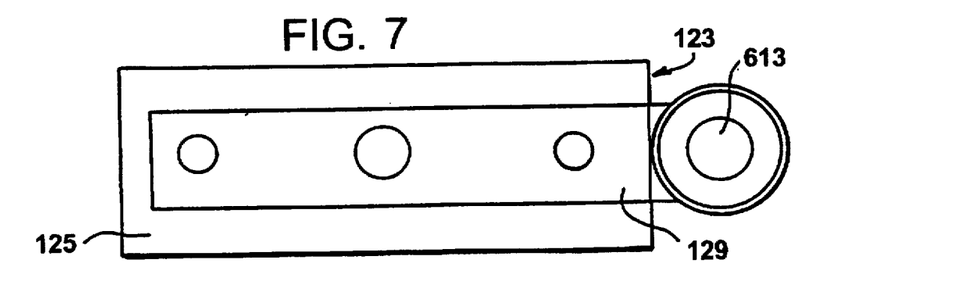
FIG. 7 is a bottom perspective view of the sample-probe cap embodying features of the present invention illustrated in FIG. 5.

Turning first to cap 123, cap 123 includes a housing 125 which is molded with a first probe containment area 127a, a second probe containment area 127b, and a sample containment area 128. The first probe containment area 127a, second probe containment area 127b and the sample containment area are cylindrical in shape and have two circular ends. As best seen in FIG. 6 and FIG. 7, one end of each probe containment area 127a and 127b is enclosed by a breakable wall of plastic or foil represented by the numeral 130. The other end of first probe containment area 127a and second probe containment area 127b is comprised of a foil seal 129. Foil seal 129 is affixed to the housing 125 after the probe solutions are placed within the first probe containment area 127a and the second probe containment area 127b.

Figure 9:
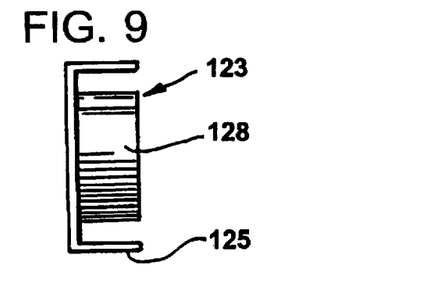
FIG. 9 is a side cross-sectional view of the sample probe cap illustrated in FIG. 5.

Sample containment area 128 has two ends in which one end is covered by foil seal 129, as best seen in FIG. 7, and the remaining end is open to receive sample, as best seen in FIGS. 6 and 9. After the sample has been placed in sample containment area 28, sample plug 131 is placed over the sample containment area and received by the cap housing 125 to sealably contain the sample within the sample containment area 128. Sample plug 131 has a breakable wail of plastic or foil 613.

Figure 8:
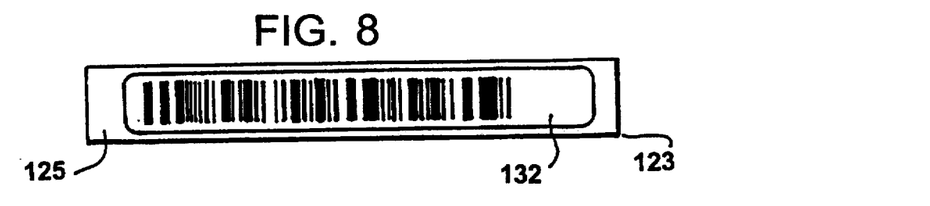
FIG. 8 is a side perspective view of the sample-probe cap embodying features of the present invention as illustrated in FIG. 5.

FIG. 8 includes a side perspective view of cap housing 125 in which a bar code 132 has been imprinted to facilitate reading of the cap type by an instrumentation reader device.

Turning now to FIG. 3, backing plate 113 includes a well housing 133. Well housing 133 is capable of receiving cap housing 125. Well housing 133 includes a first probe well 134a and a second probe well 134b. Each probe well 134a and 134b has a central opening defining a passage for the movement of fluid. Probe wells 134a and b project upwardly and are pointed to break seals 130 as the cap housing is pushed down into the well housing 133. The seals 130 pulled over and against the probe wells 134a and b to seal against the projection.

Similarly, well housing 133 includes a sample well 135 having a central opening defining a passage for the movement of fluid. Sample well 135 projects upwardly from the well housing 133 and is pointed in configuration to facilitate breaking seal 613 as the cap housing is pushed downward on the well housing 133.

As cap housing 125 is received within the well housing 133, fluids contained within the first probe containment area 127a and a second probe containment area 127b, and sample contained within the sample containment area 128 are urged through the passages of probe well 134a and b and the passage within sample well 135.

Cylindrical projections 228 extending around sample well 135 and probe wells 134a and 134b cooperate with the cylindrical forms defining containment areas 128 and 127a and to maintain and seal fluids within the containment areas and urge fluids through passages.

As illustrated, sample flows through passages of sample well 135 into a blister generally designated as 137. Probe solutions contained within the first probe area 127a flow through passages or probe well 134a into a first probe blister or chamber 138. Probe solutions contained with the second probe containment area 127b flow through probe well 134b into a second probe blister or chamber 139. After the probe and sample are placed in respective blisters, the sample well 135 and probe wells 134a and b can be sealed from the blisters by forming a permanent seal (not shown).

Vessel 111 which has a first reaction chamber 141 formed by welding permanent walls 119 thin first sheet of plastic 115 and second sheet of plastic 117. Sample and first probe solutions contained within the first probe blister 138 and sample blister 137 are urged into the first reaction chamber 141 by compressing the blister and forcing the solutions contained therein through burstable seals. Sample blister 137 is maintained separate and apart from first reaction chamber 141 by a burstable seal 142 and first probe blister is maintained separate from reaction chamber 141 by burstable seal 143. After the first probe solution and sample have entered the first reaction chamber, the first probe blister 137 and sample blister 138 can be sealed from the first reaction chamber 141 by the formation of a permanent seal.

Under hybridization conditions, the probes contained within the first probe solution are capable of binding to target. The vessel 111 contains magnetic supports to capture the probe-target complex formed. Such magnetic beads are maintained separate from the first reaction chamber 141 in a support chamber 145. Support chamber 145 includes two blistered areas to contain the bulk of the support. The support chamber 145 is maintained separate from first reaction chamber 141 by a burstable seal 147. Supports contained within the support chamber 145 are urged into the first reaction chamber 141 by compressing the chambers to urge the supports through the burstable seal 147. Target, if present, probe and support forma target-probe support complex. The magnetic supports are immobilized about the back sheet 115 and backing plate 113 by means of magnets positioned about the backing plate at positions 148a and 148b. The solutions containing sample debris are removed from the first reaction chamber 141 while the magnetic supports are immobilized. The solutions containing sample debris are urged by compressing the first reaction chamber 141 to urge solutions through passage 149 connecting the first reaction chamber 141 to effluent chamber 150.

In order to prevent back flow of solutions from the effluent chamber 150 to the first reaction chamber 141, the effluent passage 149 can be maintained closed by compressing the passage or clamping the passage.

Although much sample debris is removed by the first removal of solutions from the reaction chamber 141, sample debris may still be present in the first reaction chamber 141, nonspecifically bound to the supports and the internal structures of the chamber. In order to solubilize and suspend such further sample debris, wash solutions contained in a first wash chamber 151 are urged upon imposition of wash communication means, into the first reaction chamber 141. Wash chamber 151 is maintained separate from the first reaction chamber by means of a burstable seal 151a. Imposition of wash communication means comprises compression of the wash chamber blister 151 to urge such solutions through burstable seal 151a.

Magnetic supports containing the target-probe complex are released from the backing plate and bottom plastic sheet 115 in order to facilitate intimate contact with the wash solutions. The wash solutions are mixed with the magnetic supports by rolling solutions from end to end in the reaction chamber with a light pressure on the top plastic sheet 117. After the wash solutions have been thoroughly mixed throughout the reaction chamber 141 and the supports, the magnetic supports are again immobilized in areas 148a and 148b. Wash solutions are removed from the first reaction chamber 141 through passage 149 and into effluent chamber 150.

The magnetic supports are released and solutions from a second wash chamber 152 are allowed to enter first reaction chamber 141. Wash solutions maintained in second wash chamber 152 are urged into the first reaction chamber 141 through a burstable seal 152a by compressing the blister. Following suitable mixing, the magnetic supports maintained in first reaction chamber 141 are again immobilized and solutions removed through passage 149 to effluent chamber 150.

Similarly, the magnetic supports are released and solutions from a third wash chamber 153 are allowed to enter first reaction chamber 141. Wash solutions maintained in third wash chamber 153 are urged into the first reaction chamber 141 through a burstable seal 153a by compressing the blister. Following suitable mixing, the magnetic supports maintained in first reaction chamber 141 are again immobilized and solutions removed through passage 149 to effluent chamber 150.

In order to separate the target and probe complex from the support, vessel 111 carries eluent solutions within an eluent chamber 154. Eluent chamber 154 is maintained separate from first reaction chamber 141 by a breakable seal 154a. Compression of the eluent chamber 154 urges eluent solutions through the burstable seal 154a and into the first reaction chamber 141. Eluent solutions are mixed with the magnetic support by rolling the solutions throughout the first reaction chamber 141. Under appropriate release conditions, the target-probe complex is released from the support.

Once again, the magnetic supports are immobilized in areas generally designated by the numeral 148a and 148b. Solutions carrying the target-probe complex are urged through a breakable seal 155 separating the first reaction chamber 141 from a second reaction chamber 241.

Second reaction chamber 241 can be maintained separate from the first reaction chamber 141 by formation of a permanent wall or seal generally in the area of breakable seal 155. Second reaction chamber 241 has many features which operate in a manner identical to that described with respect to the first reaction chamber 141. Second reaction chamber 241 is in communication with a effluent chamber 250 by means of a effluent passage 249. Magnetic supports for introduction into the second reaction chamber 241 are held in a support chamber 245. Breakable seals 247 maintain the support chambers 245 separate and apart from second reaction chamber 241. Backing plate 113 includes two areas for cooperation with magnets for immobilizing magnetic supports generally designated by areas 248a and 248b. First, second and third wash chambers, respectively, are generally designated by numerals 251,252 and 253 are maintained separate and apart from the second reaction chamber 241 by means of burstable seals 251a, 252a and 253a.

Solutions held in probe blister or chamber 139 can be urged into the second reaction chamber 241 through breakable seal 140. In two-probe systems, there may be less background where the detection probe is introduced in the second reaction chamber. In the present discussion, reference to a probe-target complex is meant to include multiple probes which can be in such solutions of probe chamber 139 and probe solutions of probe blister at chamber 138.

Following recapture of the target-probe complex on supports and subsequent washes with wash solutions maintained in first, second and third wash chambers 251,252 and 253, removal of solutions through passage 249 into effluent chamber 250, the target-probe complex can be released from the second support by eluent solutions maintained in an eluent chamber 254 in a manner as that described with respect to the first reaction chamber 141. Eluent chamber 254 is maintained separate from the second reaction chamber 241 by means of burstable seal 254a.

As with the first reaction chamber, following removal of solutions from wash chambers and eluent chambers, such chambers can be permanently sealed to avoid back flow of solutions into such chambers.

Eluent solutions carrying the target-probe complex released from the support are urged through a second chamber breakable seal 255 into a third reaction chamber 341. After solutions have entered third reaction chamber 341, third reaction chamber 341 can be closed to second reaction chamber 241 by formation of a permanent wall or seal at or about the breakable seal 255.

As with the second reaction chamber, the third reaction chamber is in communication with an effluent chamber 350 through an effluent passage 349. Magnetic supports are maintained in a third support chamber 345 and enter the third reaction chamber through a burstable seal 347. A first, second and third wash chamber are maintained separate from the third reaction chamber by burstable seal 351a, 352a and 353a. An eluent chamber 354, is maintained separate and apart from the third reaction chamber 341 by burstable seal 354a. The function and operation of such components and elements is identical to the second reaction chamber. Following capture of the target-probe complex on a support and subsequent washes, the target-probe complex is released from the support. Eluent solutions containing the target-probe complex are urged through burstable seal 355 by compressing the third reaction chamber 341.

Eluent solutions containing the target-probe complex pass through burstable seal 355 into a fourth reaction chamber 441. Reaction chamber 441 is similar in structure and operation to second reaction chamber 241 and third reaction chamber 341. Reaction chamber 441 is in communication with a fourth effluent passage 449 communicating with effluent chamber 450. Magnetic supports are maintained in support chamber 445 separate and apart from the fourth reaction chamber 441 by burstable seal 447. Such supports can be immobilized within areas generally designated 448a and 448b with cooperating magnets (not shown). Wash solutions are maintained in blistered chambers 441,452 and 453 separate and apart from the fourth reaction chamber 441 by burstable seals 451a, 452a and 453a. Eluent solutions for solubilizing the target-probe complex after washes are maintained in blistered eluent chamber 454 separate and apart from the fourth reaction chamber by means of a burstable seal 454a. In the event additional washes or eluent solutions are desired, they may be carried in extra chambers 460, 461 and 462.

Following capture on supports, washes and elutions from such supports, the elution solution held in fourth reaction chamber 441 is forced through breakable seal 455 into a fifth reaction chamber 541. In order to maintain fifth reaction chamber 541 separate and apart from fourth reaction chamber 441, a permanent seal can be welded into the first and second sheets 115 and 117 along the area of burstable seal 455.

Preferably, one of the probes has a label capable of detection. Reagents to facilitate production of a detectable response are carried in detection chambers 571 and 572. In the event that the probe includes a replicatable entity, such as MDV-1-like sequences, the detection chambers 571 and 572 contain the enzyme Q-Beta replicase and necessary cofactors and agents.

Fifth reaction chamber includes a read surface 575. Read surface 575 is maintained separate from fifth reaction chamber 541 by a burstable seal 576 in order to allow complete mixing of the reagents prior to contacting the read surface 575 with the solutions. Complete mixing prior to reading signal will produce more consistent readings.

In the event that the probes include MDV-1 like sequences that are replicated by the enzyme Q-Beta replicase during a detection phase, one of the reagents of detection may include propidium iodide. Read surface 575 allows fluorescent detection of propidium iodide outside the fifth reaction chamber 541.

Embodiments of the present invention as illustrated in FIGS. 3 through 4 are capable of performing four reversible target capture cycles in a closed environment with amplification of a detectable moiety. The signal from the detectable moiety can be detected external of the vessel 111. Each vessel is contained. Solutions and apparatus for each assay are unique and are not comingled with any other assay.

While preferred embodiments have been illustrated and described, it is understood that the present invention is capable of variation in modification and, therefore, should not be limited to the precise details set forth but should include such changes and alterations that fall within the purview of the following claims.

We claim:

1. A vessel for isolating a target molecule from a sample that potentially contains the target molecule, said vessel comprising a first reaction chamber comprising a sealed cell adapted to receive the sample, a support, and a probe, and thereafter being sealed, wherein the probe is designed to specifically bind the target molecule to the support;

a wash chamber comprising a sealed cell connected to the first reaction chamber by a first burstable seal, wherein the wash chamber is arranged to deliver a wash solution through the first burstable seal into the first reaction chamber at a time when the support is immobilized in the first reaction chamber;

an effluent chamber arranged to receive wash solution and non-target molecule debris from the sample in the first reaction chamber;

an eluent chamber comprising a sealed cell connected to the first reaction chamber by a second burstable seal, wherein the eluent chamber is arranged to deliver an eluent solution through the second burstable seal into the first reaction chamber to induce release of the target molecule from the support at a time after the wash solution has passed into the effluent chamber; and a last reaction chamber arranged in series with and connected by a third burstable seal to the first reaction chamber, wherein the last reaction chamber comprises a sealed cell adapted to receive the target molecule and eluent solution from the first reaction chamber, thus isolating the target molecule from the sample.

2. A vessel of claim 1, further comprising a read chamber connected to the last reaction chamber by a fourth burstable seal, wherein the read chamber comprises a sealed cell having a read surface and is adapted to receive the target molecule and eluent solution from the last reaction chamber, and wherein the read surface transmits a detectable signal when target molecules are present in the sample.

3. A vessel of claim 2, wherein said read chamber is adapted to hold a detection reagent, which detection reagent produces a detectable signal when target molecules are present in the sample.

4. A vessel of claim 3, wherein said detection reagent comprises the enzyme Q-Beta replicase.

5. A vessel of claim 1, wherein the burstable seals comprise a point area directed against intended flow of fluid through the seal after bursting.

6. A vessel of claim 1, wherein said supports are magnetic, and can be immobilized with a magnet held outside the vessel.

7. A vessel of claim 1, further comprising a second wash chamber comprising a sealed cell connected to the first reaction chamber by a fourth burstable seal, wherein the second wash chamber is arranged to deliver a wash solution through the fourth burstable seal to the first reaction chamber at a time when the support is immobilized in the first reaction chamber.

8. A vessel of claim 1, wherein said last reaction chamber is adapted to hold an amplification reagent, which reagent amplifies any target molecules present in the sample.

9. A vessel of claim 1, wherein the vessel is formed of two sheets of plastic film heat sealed to form the separate chambers.

10. A vessel of claim 9, wherein said sheets of plastic film are comprised of a thermoplastic ionomer resin containing both covalent and ionic bonds.

11. A vessel of claim 9, wherein said two sheets of plastic film are fixed to a backing plate.

12. A vessel of claim 1, further comprising second, third, and fourth reaction chambers connected between the first and last reaction chambers in series by burstable seals located between adjacent reaction chambers, and wherein each additional reaction chamber comprises a sealed cell adapted to receive the target molecule and eluent solution from the previous reaction chamber in the series.

13. A vessel of claim 12, further comprising at least one additional wash chamber for each of said second, third, and fourth reaction chamber, wherein each wash chamber comprises a sealed cell connected directly to the respective reaction chamber by a burstable seal, and each wash chamber is arranged to deliver a wash solution through the burstable seal into the corresponding reaction at a time when the support is immobilized in the corresponding reaction chamber.

14. A vessel of claim 12, further comprising a first probe chamber arranged to receive and subsequently deliver a first probe into the first reaction chamber, wherein the first probe chamber comprises a sealed cell connected to the first reaction chamber by a fourth burstable seal; and a second probe chamber arranged to receive and subsequently deliver a second probe into the second reaction chamber, wherein the second probe chamber comprises a sealed cell connected to the second reaction chamber by a fifth burstable seal.

15. A vessel of claim 1, further comprising a first probe chamber arranged to receive and subsequently deliver a first probe into the first reaction chamber, wherein the first probe chamber comprises a sealed cell connected to the first reaction chamber by a fourth burstable seal.

16. A vessel of claim 15, further comprising a sample chamber arranged to deliver the sample into the first reaction chamber, wherein the sample chamber comprises a sealed cell connected to the first reaction chamber by a fifth burstable seal.

17. A vessel of claim 16, further comprising a well housing including a sample well, wherein the sample well comprises an open container arranged to receive and hold the sample, wherein the well housing is designed to cooperate with a cap that closes and seals the sample well, and wherein the sample well is arranged to deliver the sample into the sample chamber.

18. A sample introduction and sealing system for use with a vessel of claim 17, the system comprising a cap and a closure plug;

the cap comprising a cap housing adapted to fit slidably into the well housing of the vessel, and an open sample container having first and second ends, wherein the first end is adapted to receive the closure plug after the sample is introduced into the sample container, and the second end is sealed with a first wall; and the closure plug comprising a second wall adapted to fit slidably onto the first end of the sample container to maintain the sample in a sealed environment;

wherein at least one of the first and second walls is breakable and adapted to be pierced by the sample well on the vessel to release the sample into the sample well.

19. A sample introduction and sealing system of claim 18, wherein the vessel well housing further comprises a first probe well, and the cap further comprises a first probe container having first and second ends, wherein the first end is sealed with a wall after a first probe is introduced into the first probe container, and the second end is sealed with a breakable wall adapted to be pierced by the first probe well on the vessel to release the first probe into the first probe well.

20. A sample introduction and sealing system of claim 19, wherein the vessel well housing further comprises a second probe well, and the cap further comprises a second probe container having first and second ends, wherein the first end is sealed with a wall after a second probe is introduced into the second probe container, and the second end is sealed with a breakable wall adapted to be pierced by the second probe well on the vessel to release the second probe into the second probe well.

* * * * *